United States Patent
Verstege et al.

(10) Patent No.: US 11,257,219 B2
(45) Date of Patent: Feb. 22, 2022

(54) REGISTRATION OF STATIC PRE-PROCEDURAL PLANNING DATA TO DYNAMIC INTRA-PROCEDURAL SEGMENTATION DATA

(71) Applicant: KONINKLIJKE PHILIPS N.V., Eindhoven (NL)

(72) Inventors: Marco Verstege, Eindhoven (NL); Pieter Gerben Eshuis, Best (NL); Cherif Sahyoun, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/769,856

(22) PCT Filed: Nov. 29, 2018

(86) PCT No.: PCT/EP2018/082914
§ 371 (c)(1),
(2) Date: Jun. 4, 2020

(87) PCT Pub. No.: WO2019/110393
PCT Pub. Date: Jun. 13, 2019

(65) Prior Publication Data
US 2021/0174514 A1    Jun. 10, 2021

(30) Foreign Application Priority Data
Dec. 8, 2017 (EP) .................................. 17206113

(51) Int. Cl.
G06T 7/174 (2017.01)
G06T 7/33 (2017.01)
A61B 5/318 (2021.01)

(52) U.S. Cl.
CPC .............. *G06T 7/174* (2017.01); *A61B 5/318* (2021.01); *G06T 7/337* (2017.01);
(Continued)

(58) Field of Classification Search
None
See application file for complete search history.

(56) References Cited

U.S. PATENT DOCUMENTS

2010/0295848 A1    11/2010  Grewer et al.
2012/0046564 A1 *   2/2012  Koh ..................... A61B 5/7282
                                                          600/515
(Continued)

FOREIGN PATENT DOCUMENTS

EP            3496038 A1 *  6/2019  ............... G06T 7/33
WO     WO-2012001551 A1 *  1/2012  ............. A61B 5/065
(Continued)

OTHER PUBLICATIONS

Herlambang et al: "Real-Time Autostereoscopic Visualizaton of Registration-Generated 4D MR Image of Beating Heart"; MIAR 2008, LNCS 5129, pp. 340-358.
(Continued)

*Primary Examiner* — Jiangeng Sun

(57) ABSTRACT

Imaging systems and methods are provided, which involve acquiring static volume data using a first imaging technique; segmenting the static volume data to generate a static segmentation; annotating the static segmentation with at least one annotation; acquiring initial dynamic volume data using a second imaging technique different to the first imaging technique; segmenting the initial dynamic volume data to generate a plurality of dynamic segmentations; comparing the static segmentation to each one of the plurality of dynamic segmentations and determining, using the comparisons, a single dynamic segmentation that most closely corresponds to the static segmentation; storing the corresponding single dynamic segmentation in the memory as a reference segmentation; acquiring subsequent dynamic volume data; segmenting the subsequent dynamic volume data to generate at least one subsequent dynamic segmen-
(Continued)

tation; determining a difference between the reference segmentation and the subsequent dynamic segmentation; updating the at least one annotation using the determined difference; and displaying the at least one updated annotation together with the subsequent dynamic volume data.

15 Claims, 6 Drawing Sheets

(52) U.S. Cl.
CPC ............ *G06T 2207/10081* (2013.01); *G06T 2207/10088* (2013.01); *G06T 2207/10132* (2013.01); *G06T 2207/20224* (2013.01)

(56) References Cited

U.S. PATENT DOCUMENTS

| | | | |
|---|---|---|---|
| 2013/0102879 A1* | 4/2013 | Maclaren | A61B 5/055 600/411 |
| 2013/0211230 A1 | 8/2013 | Sperling | |
| 2017/0245936 A1 | 8/2017 | Kanade et al. | |
| 2019/0148011 A1* | 5/2019 | Rao | A61B 8/5292 600/437 |

FOREIGN PATENT DOCUMENTS

| | | | |
|---|---|---|---|
| WO | 2014031531 A1 | 2/2014 | |
| WO | 2016033065 A1 | 3/2016 | |
| WO | WO-2019219861 A1 * | 11/2019 | ............ G06T 7/33 |

OTHER PUBLICATIONS

Lang et al: "Feature Identification for Image-Guided Transcatheter Aortic Valve Implantation"; SPIE Medical Imaging,: Image-Guided Procedures, Robotic Interventions, and Modeling, 83162, Feb. 2012, pp. 83162X-1-83162X-14.
Tavard et al: Dynamic Registration of Cardiac US and CT Data Using Fourier Descriptions and Dynamic Time Warping; Image Processing Theory, Tools and Applications, IEEE, 2012, 6 Page Document.
PCT/EP2018/082914 ISR & WO.

* cited by examiner

REGISTRATION OF STATIC PRE-PROCEDURAL PLANNING DATA TO DYNAMIC INTRA-PROCEDURAL SEGMENTATION DATA

CROSS-REFERENCE TO PRIOR APPLICATIONS

This application is the U.S. National Phase application under 35 U.S.C. § 371 of International Application No. PCT/EP2018/082914, filed on Nov. 29, 2018, which claims the benefit of European Patent Application No. 17206113.7, filed on Dec. 8, 2017. These applications are hereby incorporated by reference herein.

FIELD OF THE INVENTION

The present disclosure relates to the fusion of pre-procedural static data images with intra-procedural dynamic data images. The systems and methods of the present disclosure are applicable to medical procedures such as image-guided cardiac procedures.

BACKGROUND OF THE INVENTION

This section provides background information related to the present disclosure which is not necessarily prior art.

Medical imaging is useful in many clinical applications. Different types of medical imaging exist. One type of medical imaging is ultrasound imaging. Ultrasound imaging technology is particularly useful in minimally invasive cardiac procedures, such as mitrial or tricuspid repair or replacement. For example, ultrasound imaging may involve the use of a transesophageal echocardiography (TEE) probe, which is used to image the heart and associated structures via echocardiograms in order to provide dynamic intra-procedural volume data to aid the physician during an intervention. However, it is known that ultrasound imaging does not allow for the best depiction of anatomical structures as compared to other imaging techniques.

Other types of medical imaging techniques, for example those based on Computed Tomography (CT) and magnetic resonance imaging (MRI), are known to provide better depictions of anatomical structures. However, these medical imaging techniques are generally unsuitable for intra-procedural imaging. Furthermore, the anatomical information provided by these techniques is generally static information. These imaging techniques are therefore typically used primarily for pre-procedural planning and diagnosis.

If CT or MRI-based imaging techniques are used in a planning phase prior to an intervention and then ultrasound imaging is used during the intervention, the physician must make a mental registration of the static information acquired from the planning phase to the dynamic information acquired during the intervention. This mental registration demands working memory from the physician, which requires extra effort. Furthermore, the mental registration may be inaccurate. Still further, a mental registration is particular complicated for a moving anatomy, which is commonly encountered in cardiac procedures.

US 2010/0295848 A1 discloses a system for combining images acquired from different imaging techniques.

Accordingly, it is desirable to obtain a system in which both static information and dynamic information is made available to the physician during the course of an intervention in an improved manner as compared to the prior art.

SUMMARY OF THE INVENTION

Systems and method are provided for registering planning data to intra-procedural data. According to a first aspect, there is provided an image processing device.

The imaging system includes: a processor module; a memory module; a display and an input interface configured to receive image data from a patient and transmit the image data to the processor module. The image data to be received may comprise static volume data, initial dynamic volume data and subsequent dynamic volume data. The processor module is configured to: segment the static volume data to generate a static segmentation; segment the initial dynamic volume data to generate a plurality of dynamic segmentations; compare the static segmentation to each one of the plurality of dynamic segmentations; determine, using the comparisons, a single dynamic segmentation that most closely corresponds to the static segmentation; and store the corresponding single dynamic segmentation in the memory as a reference segmentation. The processor module is further configured to: automatically segment the acquired subsequent dynamic volume data to generate a subsequent dynamic segmentation; determine a difference between the reference segmentation and the subsequent dynamic segmentation; update at least one annotation associated with the static segmentation using the determined difference; and transmit the subsequent dynamic volume data and the updated at least one annotation to the display for displaying together on the display.

Alternatively, the image processing device itself is not provided with a display; instead, a display signal representing an image of the subsequent dynamic volume data and updated annotation may be provided to an output and transferred to an external display for viewing.

Combining images related to the initial volume data and the static segmentation with the above registration technique is more accurate than other types of image fusion techniques, such as landmark anchoring. Furthermore, the above registration technique is less prone to systematic errors, such as landmark drifting. Still further, the above technique allows for the dynamic updating of annotations associated with the static segmentation.

In an embodiment, the processor module is configured to transmit the subsequent dynamic volume data to the display such that the at least one updated annotation is displayed overlaid on the subsequent dynamic volume data.

In an embodiment, the at least one annotation associated with the static segmentation is stored in the memory to be overlaid over images obtained by a third imaging technique, different from the first and second imaging techniques. The overlay of the at least one annotation on images obtained by a third imaging technique may be performed via an additional, separate registration between the second and third imaging data. This registration technique may be the same registration technique as outlined above. Alternatively, the registration technique may be a probe detection algorithm. In an embodiment, the third imaging technique is an X-ray imaging technique. In this embodiment, the registration technique employed by the processor module is a probe detection algorithm that tracks the location of the probe in the patient space from X-ray image data.

It will be appreciated that, where a third imaging technique is utilized and an additional registration algorithm as set out above is used to combine the at least one annotation with the third imaging technique, the dynamic segmentations of the additional registration algorithm acts as a 3D dynamic "bridge" between the 3D static planning data and 2D live dynamic data.

In an embodiment, the processor module is configured to use a point-based registration algorithm to determine the corresponding single dynamic segmentation that most closely corresponds to the static segmentation.

In an embodiment, the processor module is configured to automatically generate the at least one annotation associated with the static segmentation.

Examples of annotations include meshes, subsets of the total mesh, virtual devices, measurements, planned trajectories, identified anatomical targets and critical structures that are invisible, or not clearly visible, with the dynamic imaging technique. The annotations may be displayed in various forms, such as triangles, circles, gridded meshes, lines, etc.

In an embodiment, the processor module is configured to use a model-based generation algorithm to segment the static volume data to generate the static segmentation.

In an embodiment, the processor module is configured to use a model-based generation algorithm to segment the dynamic volume data to generate the dynamic segmentations.

In an embodiment, the imaging system further comprises an ECG monitor, and the processor module is configured to correlate the acquired dynamic volume data with the periods of the cardiac cycle based on an output of the ECG monitor. In one embodiment, the processor module is configured to segment the initial dynamic volume data and then store the dynamic segmentation in the memory. The processor module is also configured to store the output of the ECG monitor. The processor module is then configured to synchronize the stored dynamic segmentation with the stored output of the ECG monitor in order to determine the phase of the cardiac cycle in which the initial dynamic volume data was acquired. This technique may be used when the processing power of the processor module is not enough to generate real-time segmentations and when the cardiac phase in unknown. In situations where the processing power of the processor module is enough to generate substantially real-time segmentations, or where the cardiac phase is known, the storage of dynamic segmentations for later synchronization with a stored output of the ECG monitor is unnecessary.

In an embodiment, the processor module is configured to, prior to segmenting the acquired subsequent dynamic volume data, transmit the initial dynamic volume data to the display for displaying on the display together with at least one annotation associated with the static segmentation.

In an embodiment, the processor module is configured to display the initial volume data in the form of the reference segmentation.

In an embodiment, the processor module is configured to transmit initial volume data to the display such that the at least one annotation associated with the static segmentation is displayed as overlaid on the initial volume data.

According to a further aspect, there is provided an imaging system comprising an embodiment of the image processing device as described herein and an imager configured to acquire the initial and subsequent dynamic volume data.

In an embodiment, the imager comprises an ultrasound imager, for example an ultrasound probe.

In the embodiment where the imager is an ultrasound imager, such as an ultrasound probe, the registration algorithm may be limited to points that are inside the 3D ultrasound cone of the imager probe. Limiting the registration algorithm to using only those points that are inside the 3D ultrasound cone improves the registration algorithm accuracy.

In an example, the static volume data, for example MR or CT image data, may be receivable from an image database, such as a PACS system. Alternatively or in addition, the imaging system further comprises a pre-procedural imager for acquiring the static volume data, such as a CT or MRI imaging device.

In the following, X-ray, ultrasound, CT and MRI imaging are also referred to as "imaging modalities".

According to a further aspect, there is provided a computer-implemented imaging method comprising the steps of: acquiring static volume data using a first imaging modality; segmenting the static volume data to generate a static segmentation; annotating the static segmentation with at least one annotation; acquiring initial dynamic volume data using a second imaging technique modality to the first imaging technique; segmenting the initial dynamic volume data to generate a plurality of dynamic segmentations; comparing the static segmentation to each one of the plurality of dynamic segmentations and determining, using the comparisons, a single dynamic segmentation that most closely corresponds to the static segmentation; storing the corresponding single dynamic segmentation in the memory as a reference segmentation; acquiring subsequent dynamic volume data; segmenting the subsequent dynamic volume data to generate at least one subsequent dynamic segmentation; determining a difference between the reference segmentation and the subsequent dynamic segmentation; updating the at least one annotation using the determined difference; and displaying the at least one updated annotation together with the subsequent dynamic volume data.

In an embodiment, this annotation is automatically or semi-automatically introduced. In an alternative embodiment, a physician may introduce this annotation.

In an embodiment, the subsequent dynamic volume data is displayed in the form of the subsequent dynamic segmentation.

In an embodiment, the method further comprises the step of, prior to acquiring subsequent dynamic volume data, displaying the initial dynamic volume data together with at least one annotation associated with the static segmentation.

In an embodiment, the initial volume data is displayed in the form of the reference segmentation.

In an embodiment, at least some of the initial dynamic segmentations correspond to different cardiac phases of a patient.

In a further aspect, a computer program product is provided comprising sets of instructions which, when executed on a processing unit, cause a computing device to carry out the steps of an embodiment of the method as described herein. For example, an image processing device as described herein may correspond to such computing device, whereby the computer program is executed by the processor module of the image processing device.

These and other aspects of the present invention will become apparent from and be elucidated with reference to the embodiments described hereinafter.

BRIEF DESCRIPTION OF THE DRAWINGS

The exemplary embodiments will hereinafter be described in conjunction with the following drawing figures, wherein like numerals denote like elements, and wherein.

DETAILED DESCRIPTION OF EMBODIMENTS

Figure 1:
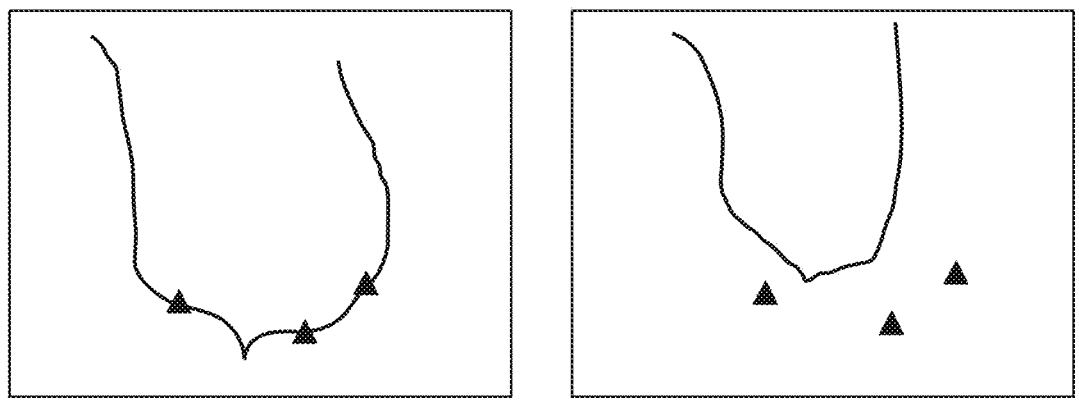
FIG. 1 is a representation showing how information associated with static planning images may be superimposed onto dynamic images.

The following detailed description is merely exemplary in nature and is not intended to limit the application and its uses. Furthermore, there is no intention to be bound by any expressed or implied theory presented in the preceding technical field, background, summary or the following detailed description. As used herein, the term "module" refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the systems described herein are merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the "connecting lines" shown in the various figures contained herein are intended to represent example functional relationships between the various modules. It should be noted that many alternative or additional functional relationships, or even physical connections, may be present in an embodiment of the present disclosure.

Embodiments of the present invention provide for the registration and image fusion of both static pre-procedural data and dynamic inter-procedural image data during an intervention. Specifically, embodiments of the invention provide for a system in which static pre-procedural data (which may be acquired using CT or MRI-based imaging techniques) is registered to dynamic inter-procedural image data (which may be acquired using ultrasound imaging techniques) and is then presented to a physician together in the form of a fused image.

In particular, the inventors recognized that there are situations where the registration between static pre-procedural data and the dynamic intra-procedural data may result in a mismatch between these data sets.

Although the following description will be explained with respect to minimally invasive cardiac interventions, it will be appreciated that the systems and methods disclosed herein are applicable to other types of interventions.

The heart has multiple systolic and diastolic cardiac phases. As the heart progresses through these different cardiac phases, it changes shape. During the pre-procedural planning stage, static pre-procedural planning information may be annotated to include planning annotations or measurements. Since the planning information is static, the annotations associated with this information correspond to structures of the heart in one cardiac phase. If the planning information is displayed together with dynamic information acquired during a different cardiac phase, there would be a mismatch due to the differences in shape of the heart between these cardiac phases.

Figure 7:
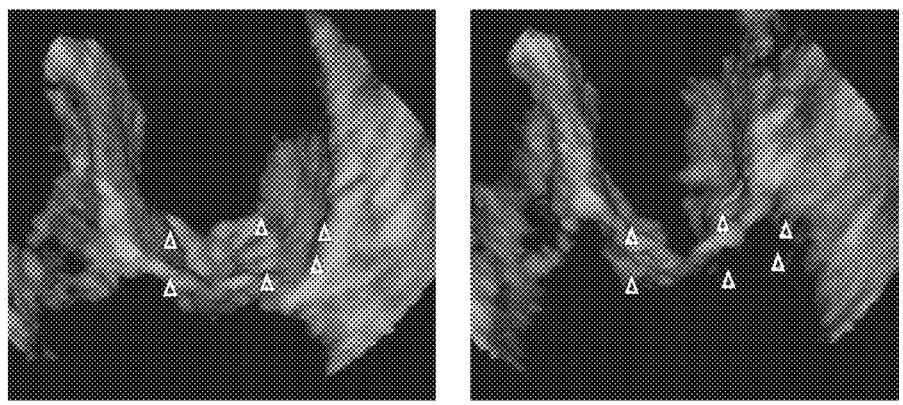
FIG. 7 is a photograph associated with the representation of FIG. 1.

For example, referring to FIG. 1, planning annotations corresponding to a static planning image is shown as superimposed on top of dynamic image data, the planning annotations being shown with triangles and the dynamic image data being shown with a line. It will be appreciated that other representations may be used to show the annotations, such as circles, gridded meshes, lines, or the like. The planning annotations correspond to a cardiac phase, which is the cardiac phase at which a pre-procedural imaging scan (such as a CT or MRI scan) was performed. As can be seen on the left of FIG. 1, the planning annotations are in the correct position when the annotations are registered to dynamic image data that has the same cardiac phase as the cardiac phase at which pre-procedural CT or MRI scan was performed. However, as can be seen on the right of FIG. 1, when the cardiac phase changes during the intervention, the dynamic image data will change, resulting in a mismatch between the dynamic image data (which has changed) and the planning annotations (which have not changed). FIG. 7 shows a photographic image corresponding to the technique used in FIG. 1.

Embodiments of the present invention prevent such a mismatch between planning annotations and live image data because of changing cardiac phases. Specifically, embodiments of the present invention allow for the dynamic updating of planning annotations to compensate for the change in shape of the heart between different cardiac phases.

Figure 2:
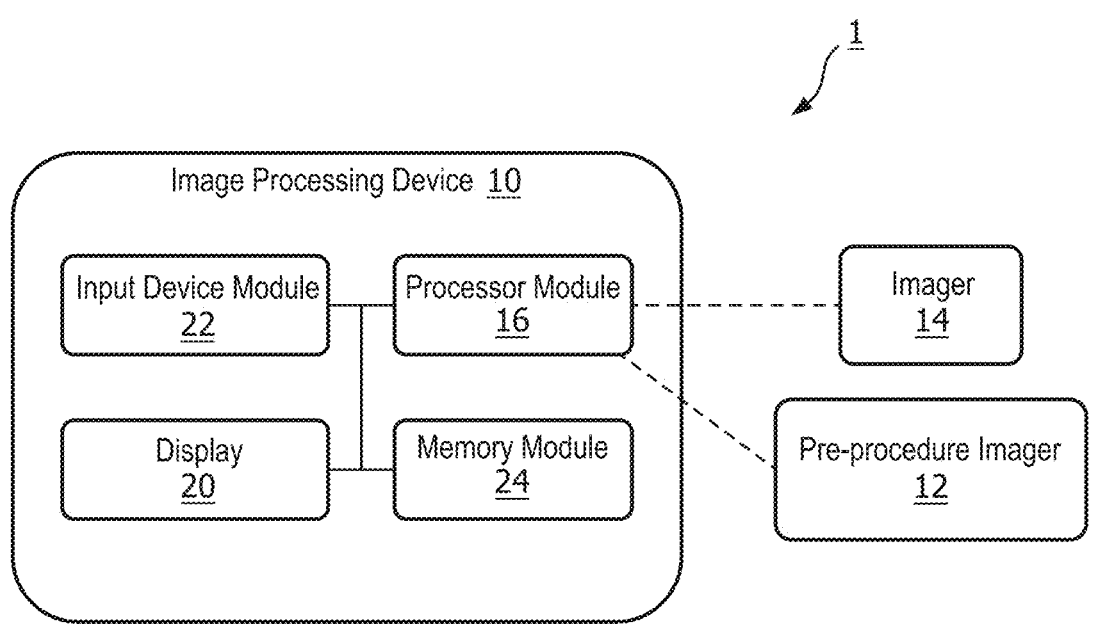
FIG. 2 is an overview of a medical imaging system in accordance with various embodiments.

FIG. 2 illustrates an example of a system 1 in accordance with embodiments of the present invention. The system 1 of FIG. 2 includes a memory 24, upon which memory 24 pre-procedural static data may be stored. The pre-procedural static data may be acquired via a pre-procedure imager 12. The pre-procedural static data may be static volume data. The static volume data may correspond to a 3D image, such as a 3D image of the heart.

The system 1 also includes a processor module 16. Although only one processor module 16 is shown, the system 1 may include multiple processing modules to provide the desired functionality. The processor module 16 is configured to perform a segmentation of the pre-procedural static data stored on the memory 24. This segmentation may be an automatic, model-based segmentation, or may alternatively be a semi-automatic, model-based segmentation which generates a segmentation based, at least in part, upon physician input.

Model-based segmentations of static volume data are known. One type of model-based segmentation involves the use of a segmentation model. The segmentation model is derived from a standard model of the organ to be segmented, or is copied from a previous segmentation. The segmentation model shares some positional features with the intended new segmentation, and certain relationships between certain features of the model segmentation and the intended new segmentation may be conserved between segmentations.

In an embodiment, the segmentation model is a multi-compartment triangulated mesh made of vertices, which vertices are connected in triangles. The segmentation model mesh encloses the anatomical regions of the model. For example, where the segmentation model is a model of a heart, the reference segmentation mesh might enclose the ventricles and atria of the heart, the myocardium around the left ventricle, and the pulmonary artery and veins.

The processor module 16 automatically segments the pre-procedural static data based on the segmentation model.

In particular, the static pre-procedural data may be segmented by the processor module 16 to generate a 3D image. This 3D image may correspond to a 3D representation of the heart. After reconstruction of the 3D representation, the processor module 16 is configured to automatically registers the 3D representation with the segmentation model. In other words, the 3D image representation is mapped onto the vertices of the segmentation model, such that the anatomical regions of the model are registered with the anatomical regions of the 3D image representation. The result of this registration is a static segmentation of the static pre-procedural data.

Annotations are then provided to the static segmentation. These annotations may be provided to the static segmentation automatically by the processor module 16 based on the segmentation model, or may be provided by the physician via an input device module 22, such as a mouse or keyboard. The annotations are registered to the static segmentation via the volume data. In other words, the position of the annotations with respect to nearby vertices of the static segmentation is determined and stored in the memory 24. These annotations may describe various areas of interest. For example, the position and size of an area to be surgically treated may be outlined with annotations demarcations. The annotations may be used by the physician to plan the intervention procedure. The position of the annotations with respect to the static segmentation may be displayed on a display 20. The input device module 22, the processor module 16, the display 20, and the memory module 24 may all be combined in an image processing device 10. Alternatively, the various elements may be located separately.

An imager 14 may also be provided. The imager 14 is for acquiring image data during the intervention. The imager 14 may be an ultrasound imager, such as a TEE or TTE ultrasound probe.

During an intervention, the imager 14 is used to acquire initial dynamic image data from the patient. Where the imager 14 is an ultrasound imager, the initial dynamic image data may correspond to live image data acquired from echocardiograms.

The initial dynamic image data acquired by the imager 14 may be in the form of a series of frames of live dynamic 3D images that correspond to different phases of an organ. Where the heart is being imaged, the dynamic image data may include a series of frames of 3D images that correspond to different phases of the cardiac cycle. The 3D image frames may normally be acquired using the ultrasound probe alone. However, the imager 14 may be used in conjunction with a conventional ECG monitor. In this embodiment, the ECG monitor is used to detect the cardiac phase, and the ultrasound image data may be synchronized with the ECG monitor data to determine in which cardiac phase a particular frame of ultrasound image data is acquired. Additionally or alternatively, other meta data associated with the dynamic volume data may be used to determine in which cardiac phase a particular frame of ultrasound image data is acquired.

The image processing device 10 has an input interface (not shown) for receiving static and dynamic volume data. During an intervention, the dynamic image data may be received directly from imager 14. The static image data is for example received from a database, such as a PACS system. Alternatively, the static image data may be received directly from a pre-procedure imager 12.

Figure 3:
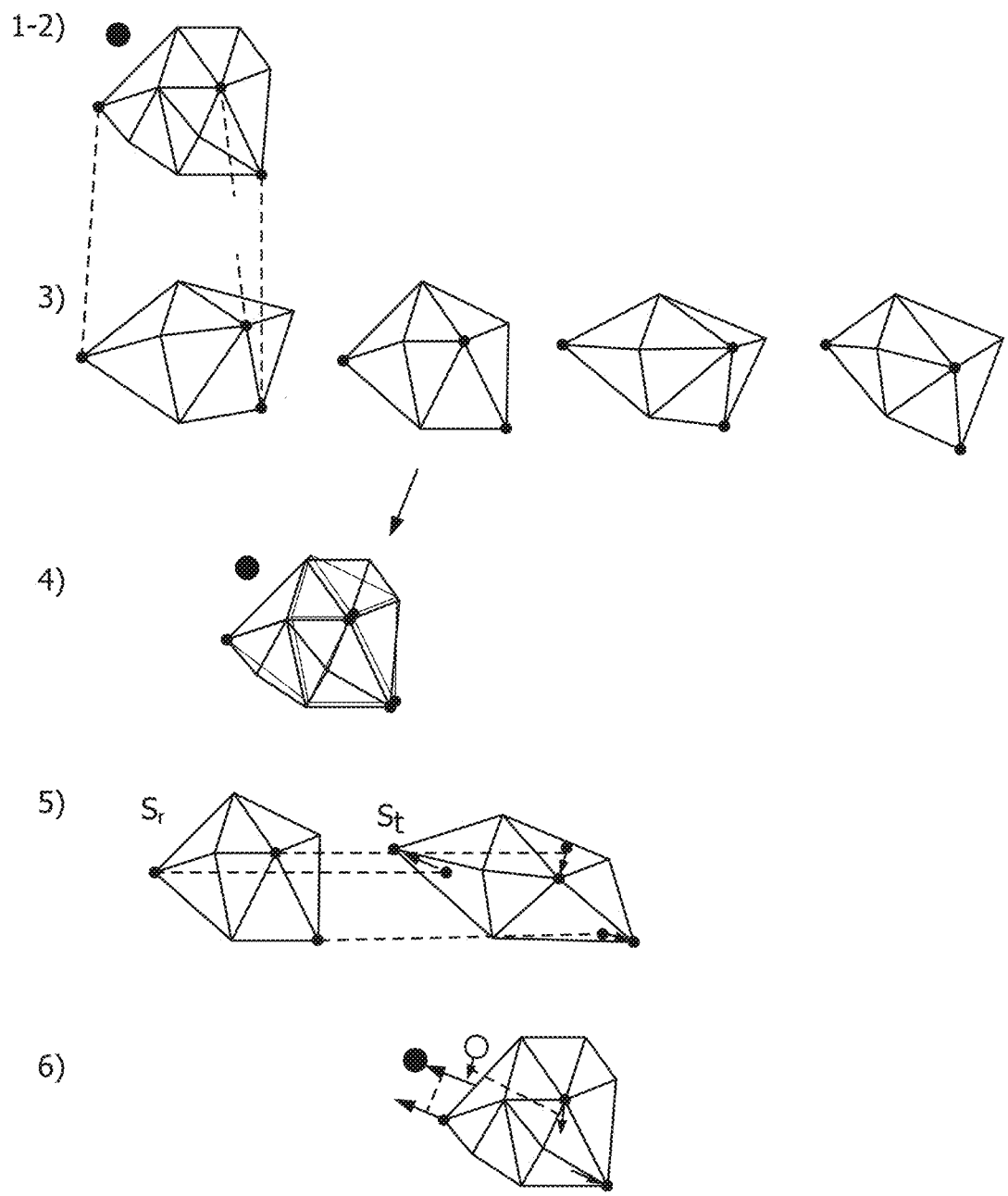
FIG. 3 is schematic illustration of a registration between static segmentation data and dynamic segmentation data in accordance with various embodiments.

Referring now to FIG. 3, the process of segmenting and registering the acquired data will now be described. As shown in FIGS. 3 (1) and (2), a static segmentation $S_s$ is generated and annotated from static image data, in the manner described above.

As shown in FIG. 3 (3), the processor module 16 is configured to automatically segment the acquired dynamic data to form a series of dynamic segmentations. These dynamic segmentations may be generated using the same model-based segmentation method as used to generate the static segmentation, or may be generated using a different segmentation technique. If a different segmentation technique is used, there should be a mapping available between the generated segmentations. For example, if a different model-based segmentation technique is used to automatically segment the frames of the 3D images acquired during the intervention in order to generate the dynamic segmentations, there should be a mapping available between the models used in the different segmentation techniques such that the vertices of the dynamic segmentations may be mapped onto the vertices of the static segmentation.

After the dynamic segmentations have been generated, the processor is configured to perform a registration between each one of the dynamic segmentations and the static segmentation. The registration may be a point-based registration. In a point-based registration, each one of the dynamic segmentations is mapped onto the static segmentation. The degree of correspondence between the vertices of the static segmentation and the vertices of each one of the dynamic segmentation is then calculated. The dynamic segmentation with the smallest error in registration $R_r$ with the static segmentation (i.e., the dynamic segmentation that has the highest degree of corresponding vertices with the static segmentation) is determined to be the dynamic segmentation that was acquired in the same cardiac phase as the data upon which the static segmentation is based. In other words, by determining which dynamic segmentation most closely corresponds to the static segmentation, the cardiac phase in which the pre-procedural image data was acquired can be determined.

Alternatively or additionally, if cardiac phase information about both of the static and dynamic segmentations is available, this cardiac phase information may be used by the processor module to determine which dynamic segmentation most closely corresponds to the static segmentation.

After the determination of the dynamic segmentation which most closely corresponds to the static segmentation, this dynamic segmentation is stored in the memory 24 as a reference segmentation $S_r$.

After determination and storage of the reference segmentation $S_r$, the initial dynamic volume data may be displayed on the display 20. This initial dynamic volume data may be displayed in the form of the reference segmentation, or in another form. Alternatively, the initial dynamic volume data may not be displayed on the display. If it is to be displayed, the initial dynamic volume data may be displayed together with the static segmentation, or aspects of the static segmentation. In particular, since the registration determines the dynamic segmentation that most closely corresponds to the static segmentation, aspects of the reference segmentation and the static segmentation may be fused by matching vertices of the static segmentation with the vertices of the reference segmentation, as shown in FIG. 3 (4). Certain aspects of the combination of the reference segmentation and the static segmentation may then be displayed on the display 20.

In particular, the annotations applied to the static segmentation may be displayed as overlaid on top of the initial dynamic volume data. Since it has been determined that the reference segmentation was generated based on image data acquired during the same cardiac phase as the image data upon which the static segmentation is based, the location of the annotations will not be adversely affected by the difference in the shape of the heart between cardiac phases. In other words, since the reference segmentation and the static segmentation are based on data acquired during the same cardiac phase, the annotations associated with the static segmentation can be overlaid on top of the reference segmentation, or the initial dynamic volume data from which the reference segmentation is generated, without the locational "mismatch" errors as shown in FIG. 1 occurring. As such, the annotations and/or measurements may be registered to the reference segmentation in order to guide the physician during the intervention.

After the acquisition of the initial dynamic image data and the determination of the reference segmentation $S_r$, subsequent frames of dynamic image data are acquired by the imager 14. These further dynamic image data frames are segmented by the processor module 16 to generate further dynamic segmentations $S_t$.

The processor module 16 is configured to compare each one of the generated further dynamic segmentations $S_t$ to the reference segmentation $S_r$. Specifically, the processor module 16 is configured to map the change in the vertex positions between a subsequent dynamic segmentation $S_t$ and the reference segmentation $S_r$, as shown in FIG. 3 (5).

The change in the vertex positions between the reference segmentation $S_r$ and a subsequent dynamic segmentation $S_t$ is then used to determine the change in the shape of the heart. This change may be due to the heart being in a different cardiac phase from the phase at which the reference segmentation was acquired, or may be due to a different physiological reason.

The processor module 16 is configured to use the mapped change in the vertex positions between the reference segmentation $S_r$ and the subsequent dynamic segmentation to determine how the annotations and/or measurements associated with the static segmentation should be correctly transformed to correspond to the same location on the subsequent dynamic segmentation.

For example, as can be seen in FIG. 3 (6), if an annotation associated with the static segmentation was close to a group of nearby vertices on the static segmentation, that annotation should also be close to a corresponding group of nearby vertices on the reference segmentation $S_r$, and would be registered to these same vertices on the reference segmentation $S_r$. If a subsequent dynamic segmentation included an arrangement of these vertices which were translated in a particular direction with respect to the corresponding vertices of the reference segmentation $S_r$, the processor module 16 would determine that the annotation associated with these vertices should also be translated based on the vertices' translation.

In this manner, the annotation positions may be dynamically updated for each subsequent dynamic segmentation based on the mapped vertex translations. The updated annotation positions are then be displayed on the display 20 as overlaid on the subsequent dynamic volume data. The subsequent dynamic volume data may be displayed in the form of the subsequent dynamic segmentation. As such, the original annotations associated with the static segmentation are dynamically updated for subsequent dynamic segmentations. This dynamic updating of the annotations reduces the problem of mismatches between the annotation and measurement positions due to movement of the vertices of the imaged organ, which movement may be due to, for example, the heart moving into a different cardiac phase.

Additional image fusing techniques may be used to combine aspects of the static segmentation with the dynamic segmentation. For example, in addition to using the registration to overlay the annotations on the dynamic volume data, landmark anchoring techniques such as speckle tracking may be used to combine these images. Although the registration algorithm results in a more accurate image fusion than conventional landmark anchoring techniques, which techniques are prone to annotation drifting, landmark anchoring techniques may be used in addition to the registration algorithm in order to "fine-tune" the image fusion.

Furthermore, the transformation of the annotation based on the translation of nearby vertices may be dependent upon the distance of the respective vertices to the annotation. For example, the transformation algorithm may assign an influence rating to nearby vertices, with the influence of each particular vertex decreasing as the distance between that vertex and the annotation increases. When the vertex translations between the reference segmentation and subsequent dynamic segmentations are determined, the amount of the transformation of the position of the annotation is dependent upon the influence rating of the vertex. Specifically, the translation of higher influence vertices carries a greater weight in the determination of the transformation of the position of the annotation than the translation of lower influence vertices. In this manner, the accuracy of the transformation of the annotation position for subsequent dynamic annotations may be improved.

Figure 4:
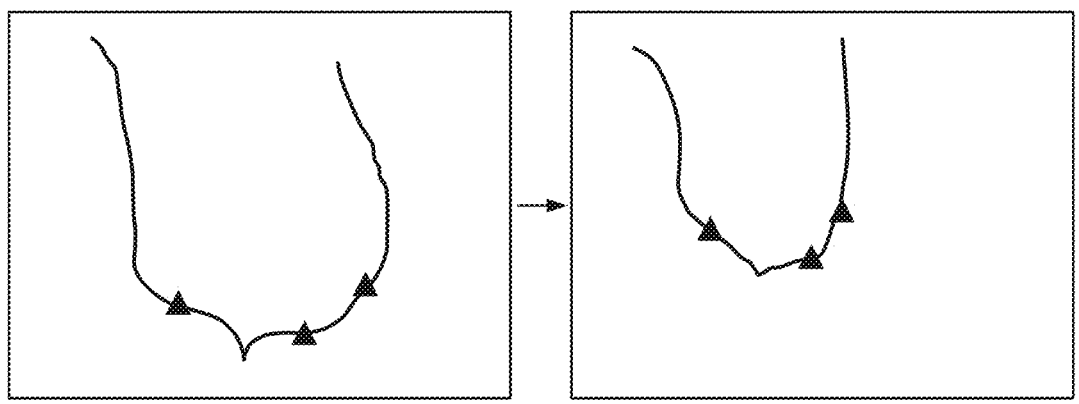
FIG. 4 is a representation showing how information associated with static planning images may be dynamically updated and then superimposed onto dynamic images in accordance with various embodiments of the invention.
Figure 8:
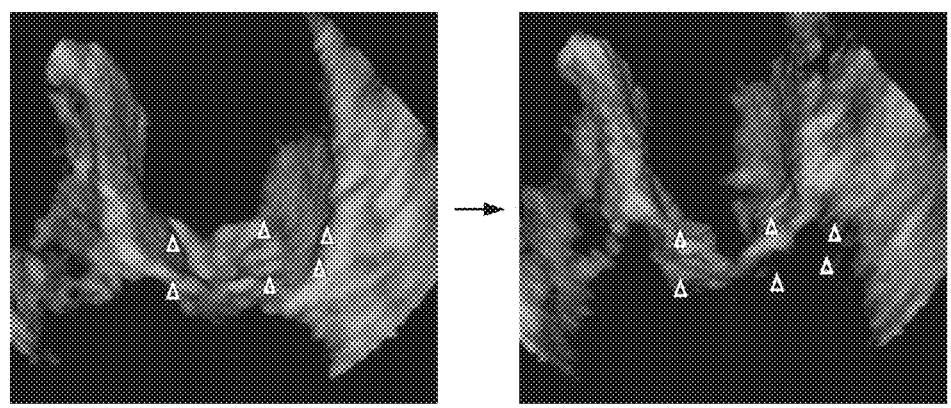
FIG. 8 is a photograph associated with the representation of FIG. 4.

An example of the dynamic updating of annotations in reaction to a change in cardiac phase can be seen in FIG. 4. Here, the same annotations for the same static segmentation as was used in FIG. 1 are overlaid on top of a dynamic segmentation on the left side of FIG. 4. For the subsequent dynamic segmentation on the right side of FIG. 4, the heart is in a different cardiac phase. However, since the annotation has been dynamically updated based on the mapped vertex change between the initial dynamic segmentation and the subsequent dynamic segmentation, the annotation correctly corresponds to the annotated location on the subsequent dynamic segmentation. FIG. 8 shows the photographic image corresponding to the technique according to embodiment of the invention represented in FIG. 4.

Figure 5:
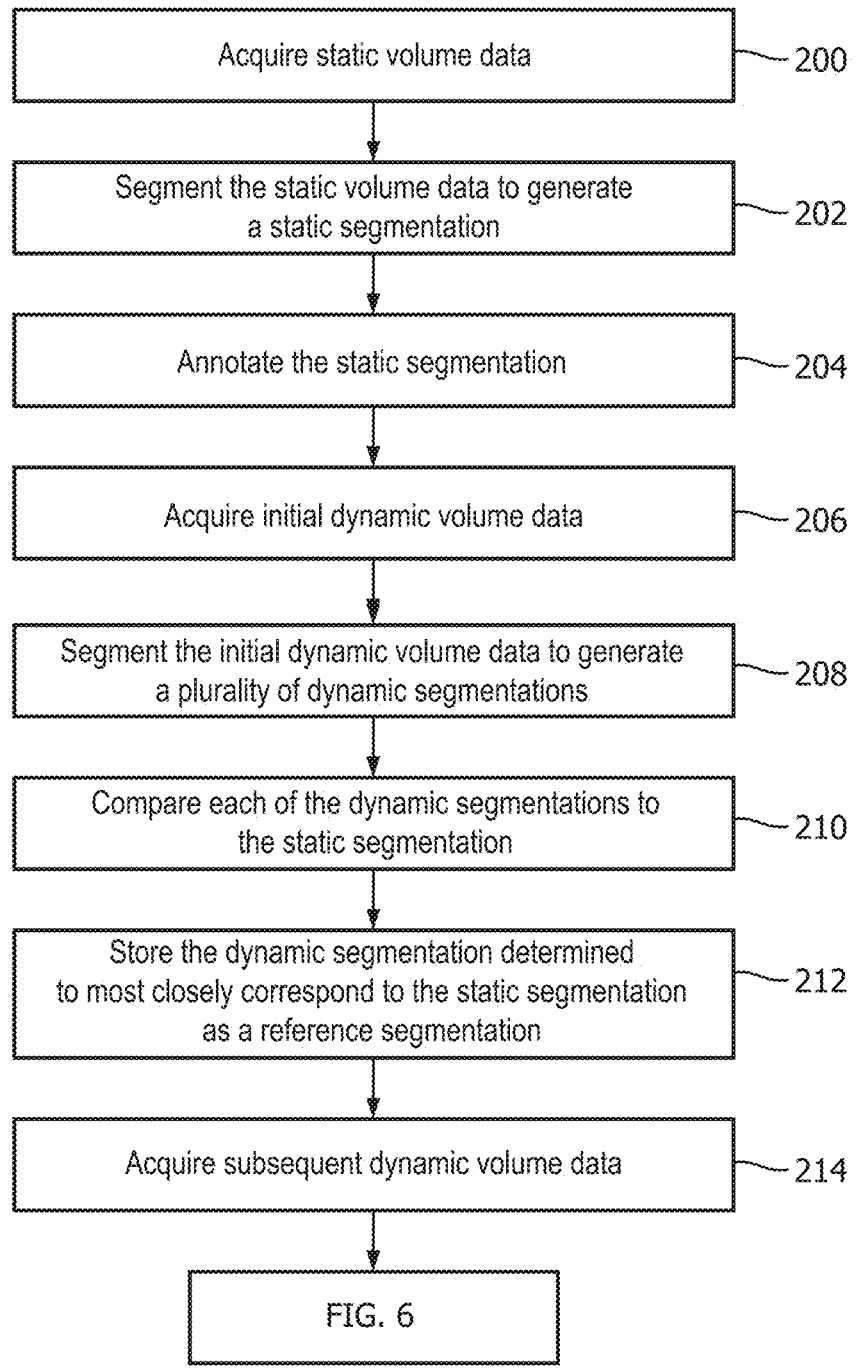
FIG. 5 is a flowchart illustrating a method in accordance with various embodiments.
Figure 6:
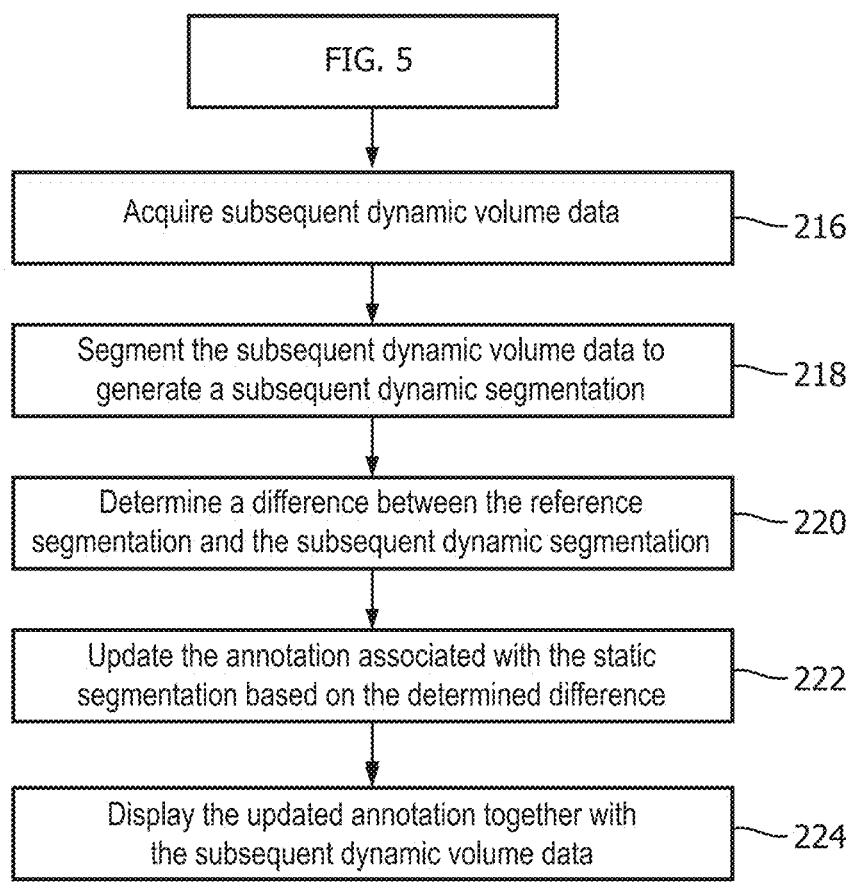
FIG. 6 is a flowchart illustrating additional method steps that may be performed in the method shown in FIG. 5.

Turning now to FIGS. 5 and 6, a flowchart illustrating a computer-implemented method in accordance with embodiments of the invention are shown. At step 200, static volume data is acquired using a first imaging technique, such as MRI or CT imaging. At step 202, the static volume data is segmented to generate a static segmentation. At step 204, the static segmentation is annotated with at least one annotation. The annotating of the static segmentation may be automatic, semi-automatic, or manual. At step 206, initial dynamic volume data is acquired using a second imaging technique different to the first imaging technique. The second imaging technique may be ultrasound imaging, for example ultrasound imaging using a TEE probe. At step 208, the initial dynamic volume data is segmented to generate a plurality of dynamic segmentations. At step 210, each one of the plurality of dynamic segmentations is compared to the static segmentation in order to determine which one of the dynamic segmentations most closely corresponds to the static segmentation. This comparison may be performed using a registration algorithm, for example a point-based registration algorithm that determines the proximity of the vertex locations of each one of the dynamic segmentations to the vertex locations of the static segmentation. At step 212, the dynamic segmentation which is determined to most closely correspond to the static segmentation is stored in the memory as a reference segmentation $S_r$. At step 216 subsequent dynamic volume data is acquired. At step 218, the subsequent dynamic volume data is segmented to generate at least one subsequent dynamic segmentation. At step 220, a difference between the reference segmentation and the subsequent dynamic segmentation is determined. At step 222, the annotation associated with the static segmentation is updated based on the determined different. At step 224, the updated annotation is display together with the subsequent dynamic volume data. The subsequent dynamic volume data may be displayed in the form of the subsequent dynamic segmentation.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

For example, even though the above disclosure focuses primarily on the field of cardiac surgery, the present disclosure finds applications in other fields as well. For example, the present disclosure will be useful in any medical procedure where a good registration to a segmentation of dynamic volume data is required.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing device, comprising:
a processor module;
a memory module;
a display; and
an input interface,
wherein the input interface is configured to receive image data and to transmit the image data to the processor module, the image data including:
static volume data,
initial dynamic volume data, and
subsequent dynamic volume data,
wherein the processor module is configured to:
segment the static volume data to generate a static segmentation;
segment the initial dynamic volume data to generate a plurality of dynamic segmentations;
compare the static segmentation to each one of the plurality of dynamic segmentations;
determine, using the comparisons, a single dynamic segmentation that most closely corresponds to the static segmentation;
store the corresponding single dynamic segmentation in the memory module as a reference segmentation, automatically segment the subsequent dynamic volume data to generate a subsequent dynamic segmentation;
determine a difference between the reference segmentation and the subsequent dynamic segmentation;
update at least one annotation associated with the static segmentation using the determined difference; and
transmit the subsequent dynamic volume data and the updated at least one annotation to the display for displaying together on the display.

2. The device of claim 1, wherein the processor module is configured to transmit the subsequent dynamic volume data to the display such that the updated at least one annotation is displayed as overlaid on the subsequent dynamic volume data.

3. The device of claim 1, wherein the processor module is configured to use a point-based registration algorithm to determine the corresponding single dynamic segmentation that most closely corresponds to the static segmentation.

4. The device of claim 1, wherein the processor module is configured to automatically generate the at least one annotation associated with the static segmentation.

5. The device of claim 1, wherein the processor module is configured to use a model-based generation algorithm to segment the static volume data to generate the static segmentation and to segment the dynamic volume data to generate the plurality of dynamic segmentations.

6. The device of claim 1, wherein the processor module is configured to, prior to segmenting the subsequent dynamic volume data, transmit the initial dynamic volume data to the display for displaying on the display together with the at least one annotation associated with the static segmentation.

7. The device of claim 6, wherein the processor module is configured to display the initial dynamic volume data in the form of the reference segmentation.

8. An imaging system, comprising:
an image processing device according to claim 1, and
an imager configured to acquire the initial dynamic volume data and the subsequent dynamic volume data.

9. The system of claim 8, wherein the imager comprises an ultrasound imager.

10. The system of claim 8, wherein the static volume data are MR or CT image data receivable from a database.

11. The system of claim 8, further comprising an MM imager or a CT imager as a pre-procedure imager configured to acquire the static volume data.

12. The system of claim 8, further comprising an ECG monitor, and wherein the processor module is configured to correlate the acquired dynamic volume data with periods of a cardiac cycle on the basis of an output of the ECG monitor.

13. A computer-implemented imaging method comprising:
acquiring static volume data using a first imaging modality;
segmenting the static volume data to generate a static segmentation;
annotating the static segmentation with at least one annotation;
acquiring initial dynamic volume data using a second imaging modality different from the first imaging modality;
segmenting the initial dynamic volume data to generate a plurality of dynamic segmentations;
comparing the static segmentation to each one of the plurality of dynamic segmentations and determining, using the comparisons, a single dynamic segmentation that most closely corresponds to the static segmentation;
storing the corresponding single dynamic segmentation in memory as a reference segmentation;
acquiring subsequent dynamic volume data;
segmenting the subsequent dynamic volume data to generate at least one subsequent dynamic segmentation;
determining a difference between the reference segmentation and the at least one subsequent dynamic segmentation;
updating the at least one annotation using the determined difference; and
displaying the at least one updated annotation together with the subsequent dynamic volume data.

14. The computer-implemented method of claim 13, further comprising, prior to acquiring the subsequent dynamic volume data, displaying the initial dynamic volume data together with at least one annotation associated with the static segmentation.

15. A non-transitory computer-readable storage medium having stored a computer program product comprising sets of instructions which, when executed by a processor module of an image processing device, cause the processor module to perform the method according to claim 13.

* * * * *